United States Patent [19]

Cicciu et al.

[11] Patent Number: 4,897,077
[45] Date of Patent: Jan. 30, 1990

[54] METHOD OF INSERTING AN IAB DEVICE INTO THE BODY

[75] Inventors: Gerald J. Cicciu, Sudbury, Mass.; Edward J. Lombardi, Derry, N.H.

[73] Assignee: Kontron Inc., Everett, Mass.

[21] Appl. No.: 275,593

[22] Filed: Nov. 23, 1988

Related U.S. Application Data

[63] Continuation of Ser. No. 53,178, May 22, 1987, abandoned.

[51] Int. Cl.$^4$ ............................................. A61B 19/00
[52] U.S. Cl. .................................. 600/18; 128/325; 128/343
[58] Field of Search ................. 600/18; 128/656–658, 128/325, 341, 343, 344; 604/53, 158, 164, 167, 169, 256, 264

[56] References Cited

U.S. PATENT DOCUMENTS

| | | |
|---|---|---|
| 3,633,579 | 1/1972 | Alley et al. . |
| 3,877,429 | 4/1975 | Rasumoff . |
| 3,921,631 | 11/1975 | Thompson ............................ 604/53 |
| 4,000,739 | 1/1977 | Stevens ................................. 128/656 |
| 4,149,535 | 4/1979 | Volder . |
| 4,166,469 | 9/1979 | Littleford . |
| 4,239,042 | 12/1980 | Asai . |
| 4,304,231 | 12/1981 | Bodicky et al. . |
| 4,306,562 | 12/1981 | Osborne ............................... 604/164 |
| 4,326,520 | 4/1982 | Alley . |
| 4,327,722 | 5/1982 | Groshong et al. . |
| 4,345,606 | 8/1982 | Littleford . |
| 4,362,150 | 12/1982 | Lombardi . |
| 4,371,686 | 2/1983 | Yamamoto . |
| 4,451,256 | 5/1984 | Weikl et al. . |
| 4,467,790 | 8/1984 | Schiff . |
| 4,473,067 | 9/1984 | Schiff ................................... 128/1 D |
| 4,525,157 | 6/1985 | Vaillancourt ........................ 128/658 |
| 4,540,404 | 9/1985 | Wolvek ................................ 128/1 D |
| 4,581,019 | 4/1986 | Curelaru . |
| 4,581,025 | 4/1986 | Timmermans . |
| 4,588,398 | 5/1986 | Daugherty . |
| 4,610,671 | 9/1986 | Luther . |
| 4,629,450 | 12/1986 | Suzuki et al. . |
| 4,738,658 | 4/1988 | Magro et al. ........................... 604/53 |

OTHER PUBLICATIONS

Seldinger, S., ACTA Radiologica (Stockholm), 39(5): 368–376, (May 1953).
Technical Notes, Tegtmeyer et al., vol. 139, pp. 231–232, (Apr. 1981).

*Primary Examiner*—Ruth S. Smith
*Attorney, Agent, or Firm*—George M. Gould; Bernard S. Leon; A. Kate Huffman

[57] ABSTRACT

A method for inserting an intra-aortic balloon device into a patient without using an insertion sheath is provided. Additionally, a hemostasis sheath is described for use with the insertion method. The hemostasis sheath may be incorporated onto the balloon catheter during manufacture before attachment of the intra-aortic balloon bladder. The hemostasis sheath is tapered from a smaller outside diameter at the point closest to the balloon bladder gradually increasing in diameter towards a large outside diameter at the end opposite the balloon bladder. The hemostasis sheath may also have an extended tip of constant outside diameter at its proximal end to facilitate insertion through the skin. If bleeding occurs after insertion of the intra-aortic balloon according to the invention, the hemostasis sheath is slid into the insertion site to stop the bleeding.

21 Claims, 3 Drawing Sheets

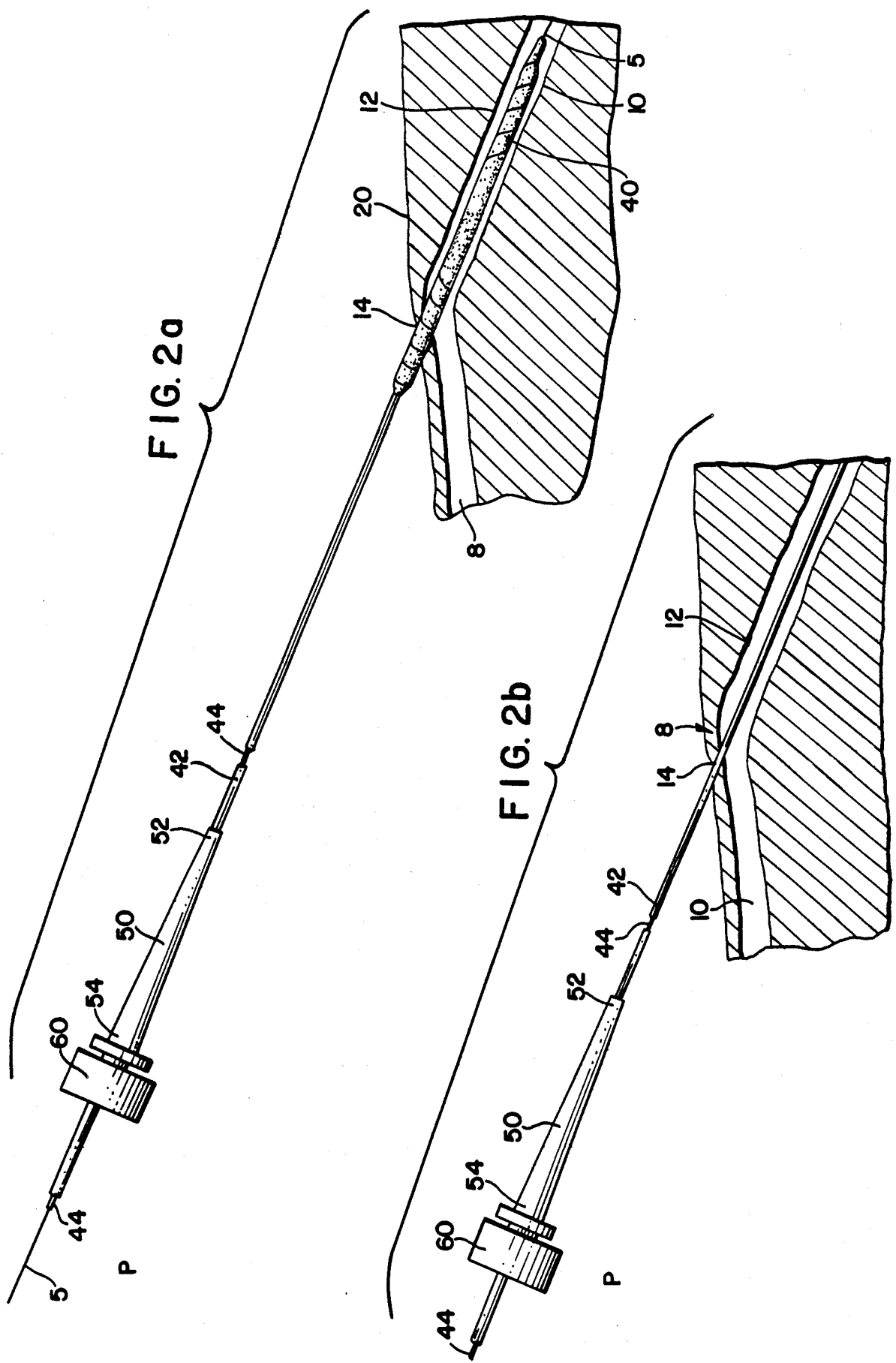

METHOD OF INSERTING AN IAB DEVICE INTO THE BODY

This application is a continuation of applicaton Ser. No. 53,178, filed May 22, 1987, now abandoned.

BACKGROUND OF THE INVENTION

1. Field of the Invention

The present invention relates to an improved method of inserting an intra-aortic balloon (hereinafter "IAB") device into the body by a sheathless insertion technique. Additionally, the invention relates to the use of a hemostasis sheath with this technique. When used in combination with the sheathless insertion technique, the hemostasis sheath facilitates use of the IAB device by lowering the degree of the obstruction in the femoral artery while controlling bleeding back through the insertion site after the IAB has been inserted.

2. Description

IAB devices are introduced into the body and are used to assist the pumping action of the heart. See, for example, U.S. Pat. No. 4,362,150. In some instances, they may remain in the body for extended periods of time, such as several days or more.

One method of installing an IAB device in the body is via a non-surgical insertion into the femoral common artery through the skin using the percutaneous insertion (Seldinger) technique.

In the prior art percutaneous insertion technique, the skin is punctured to form a hole through the skin and into the femoral artery. A short guide wire is inserted into the femoral artery and the hole is then expanded by an inserter dilator (for example, an 8-French dilator) which slides over the guide wire through the skin into the artery. The inserter dilator is removed and a series of progressively larger dilators are inserted into the hole over the guide wire to increase the size of the hole. Next an insertion sheath is passed through the hole and into the femoral artery. This sheath has an inside diameter generally corresponding to the outside diameter of the IAB to be inserted. The short guide wire is removed and is replaced by a long guide wire which is fed up through the artery to the vicinity of the aorta. The IAB is passed over the distal end of the guide wire and slides along the long guide wire up through the sheath and along the artery all the way up to the aorta.

Although the foregoing procedure generally is a safe, rapid and efficacious way of intra-aortic balloon insertion, the prerequisite insertion and use of the sheath is a step which requires time and equipment to perform, often under circumstances such that time is a critical factor to patient survival, as during cardiogenic shock.

During the foregoing described procedure, arterial bleeding through the sheath must be carefully controlled during the time interval between the removal of the short guide wire from the sheath and the insertion of the wrapped balloon over the long guide wire. Often, especially in a hypovolemic patient, this loss of blood may be critical. Also when the balloon bladder is wrapped, spiral interstices are produced along its length. The interstices of the wrapped balloon membrane do not provide for the complete occlusion of the sheath between its inner wall and the wrapped balloon. Therefore, a certain amount of arterial bleeding takes place during the time that is required to fully insert the wrapped balloon membrane portion of the balloon catheter into the blood vessel.

In some cases, the sheath may have to be withdrawn partly from the percutaneous wound to permit complete introduction of the balloon membrane into the sheath, especially in those cases of extreme vascular tortuosity. This creates an additional loss of critical time and of critical blood.

Another problem experienced with some patients, is that after IAB insertion is complete, blood flow to the lower extremities is diminished substantially. The decrease in blood flow is generally attributable to the obstruction of the femoral artery caused by the relatively large diameter of the insertion sheath extending into the artery. By removing the sheath, the obstruction in the femoral artery can be decreased substantially. Certain prior art techniques attempts to solve this concern by utilizing splittable insertion sheaths. Various types of splittable, removable insertion sheaths which would be suitable for this purpose are disclosed in the prior art. See for example, U.S. Pat. Nos. 4,166,469, 4,581,019 and 4,581,025. Once the insertion sheath is removed, there would remain the IAB catheter which connects an inflatable and deflatable bladder member of the IAB with the external pumping/monitoring equipment.

U.S. Pat. No. 4,540,404 attempts to address these concerns by using an IAB with a tapered tip and a sheath which slides over the balloon bladder to form an assembly. After insertion, the sheath can be withdrawn to expose the balloon.

However, after removal of the insertion sheath the arterial wall must constrict to seal around the balloon catheter, which has a smaller outside diameter than the insertion sheath. Therefore, in non-elastic or diseased vessels, the required vessel constriction may not always occur resulting in profuse bleeding from the insertion site between the IAB catheter and arterial puncture.

One way to stop this bleeding is to exert pressure on the artery above the insertion site. However, this has the disadvantage that it may damage the balloon catheter and requires time and an additional step in the IAB insertion process. If bleeding cannot be stopped, the IAB must be removed.

SUMMARY OF THE INVENTION

Accordingly, there has been invented an improved method for inserting an IAB device into the body in a modified percutaneous insertion technique without the use of an insertion sheath. Additionally, there is described a hemostasis sheath which is used in this method to control bleedback through the insertion site after insertion of the IAB.

In accordance with the invention, an IAB insertion technique is provided to enable insertion of an IAB device directly into a blood vessel over a guide wire, without the need first to insert and use an introducer sheath.

DESCRIPTION OF THE DRAWINGS

The invention will now be described with reference to the following drawings, which are merely exemplary and are not meant to limit the scope of the invention in any respects.

FIG. 2a is a side elevation view of an IAB device showing the IAB bladder being directly inserted into the femoral common artery without an insertion sheath according to the inventive method;

FIG. 2b is a side elevation view partly in cross-section showing the IAB device of FIG. 1 following insertion of the IAB bladder into the femoral common artery;

DESCRIPTION OF THE PREFERRED EMBODIMENT

Figure 1A:
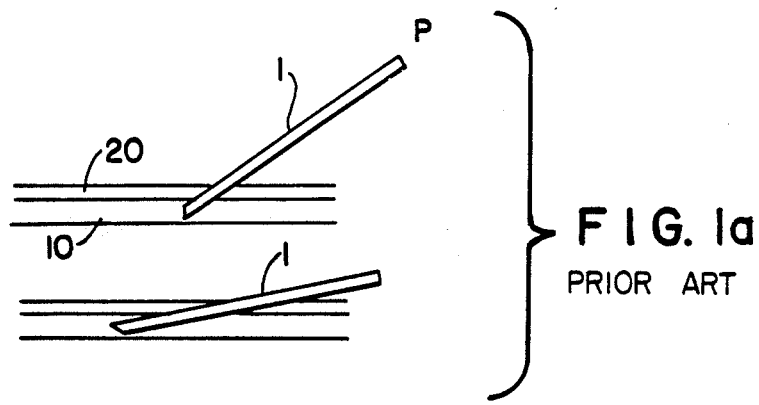
FIGS. 1a–d show in succession (a) the puncture of the skin and artery, (b) insertion of the guide wire, (c) dilation of the insertion site and (d) insertion of an insertion sheath employing a prior art (Seldinger) technique.
Figure 1B:
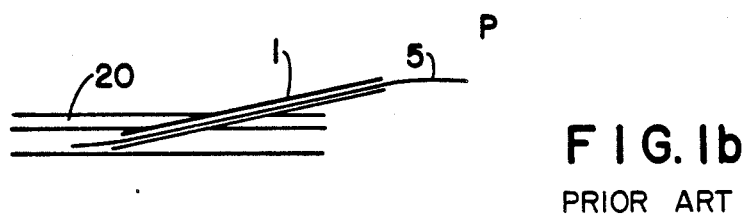
Figure 1C:
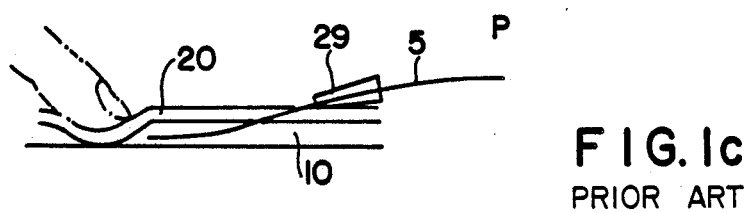
Figure 1D:
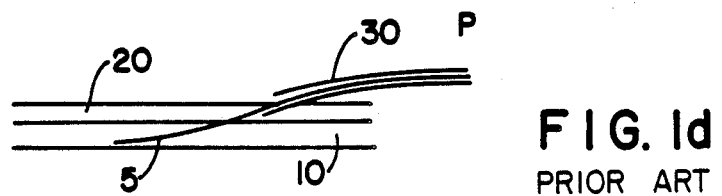

FIGS. 1a-1d shows various steps employed in the prior art (Seldinger) technique for inserting an IAB device percutaneously. There is shown needle 1, guide wire 5, dilator 29, insertion sheath 30, skin 20 and femoral artery 10. FIG. 1a shows puncture of the skin and the femoral artery using a hypodermic needle 1 (e.g. Potts cone head). FIG. 1b shows placement of a guide wire 5 into the artery through the hollow bore of the needle. FIG. 1c shows removal of the hypodermic needle 1 from the artery leaving the guide wire 5 in place and the dilation of the opening with dilator 29 (e.g., Grunzig type). Finally, FIG. 1d shows placement of an insertion sheath 30 into the artery over the guide wire following dilation of the insertion site.

With reference to FIGS. 2a, 2b and 3-6 the insertion of an IAB device into the body via a non-surgical insertion into the femoral common artery through the skin using a new percutaneous insertion technique according to the invention will be described. A physician (not shown) would be positioned in the left-hand margin in relation to the various elements being described. In FIGS. 1a-1d, FIGS. 2a, 2b, and FIG. 3, the location of the physician is designated by the symbol "P". The terms "proximal" and "distal" as used herein shall refer to position relative to that of the physician.

Referring to FIGS. 2a and 2b, the IAB device generally comprises IAB bladder 40 which is attached to balloon catheter 42. The IAB is a double lumen device with a central hollow stylette 44 and preferably of the type described in U.S. Pat. No. 4,362,150, which patent is incorporated herein by reference. The IAB can have a wrap handle for rotation as described in the above patent or can have a fixed type configuration. The hollow stylette preferably is a hypodermic tubing with a flexible segment within the balloon.

Prior to insertion, the bladder 40 is wrapped about itself to reduce its diameter either by the manufacturer or by the physician. The balloon catheter 42 may, for example, as is known in the art be attached at its proximal end to a rotating or fixed handle (not shown) and may also be connected in known manner to an intra aortic balloon pumping/monitoring system (also not shown).

The insertion technique according to the invention will now be described.

With reference to FIGS. 1a-1d and FIG. 2a, a small hypodermic needle (not shown in FIG. 2a but shown in FIG. 1a) is inserted through the skin 20 of a patient to perforate or puncture the femoral artery 10. When blood spurts from the open external end of the needle, placement of the hypodermic needle within the artery 10 is confirmed. A long guide wire 5 (e.g. up to about 150-190 cm or longer) sufficient in length to reach the central aorta is fed into the artery 10 by passing the guide wire through the center of the hollow hypodermic needle.

Next, the hypodermic needle is removed leaving the guide wire 5 in place. One or more progressively larger dilators (preferrably a single expanding, e.g. Grunzig type dilator) is then placed over the guide wire and advanced through the perforated skin 20 and into the artery 10 in order to expand the hole in order to achieve an opening large enough to permit the passage of the wrapped IAB bladder 40. For example, when using a 10.5 French IAB the hole should be dilated to approximately 10 French in diameter. Once the skin 20 and artery 10 have been fully dilated, the dilator is removed and the IAB device is inserted directly into the patient without passing it through an insertion sheath.

Still referring to FIG. 2a, the IAB bladder 40 even in its wrapped condition has a larger outside diameter than the IAB catheter 42. As a result the IAB bladder 40 will dilate the insertion site to a larger diameter than that of the catheter 42.

Reference is now made to FIG. 2b which shows, from left to right, the hemostasis sheath 50 and IAB catheter 42 of FIG. 2a with the IAB bladder 40 now inserted into the aorta (not shown).

As can be seen in FIG. 2b, the insertion site 8 after passage of the IAB, may have an opening which due to some inelasticity in the skin has not completely closed around the catheter 42. This condition may result in uncontrollable bleeding from the insertion site 8.

As a means to diminish this bleeding when it occurs, the present invention utilizes hemostasis sheath 50 which is slidably coupled to the catheter 42.

As will be discussed in more detail below, the hemostasis sheath 50 preferrably has a conical configuration and has a distal end 52 which in the preferred embodiment is only slightly larger than the outside diameter of the catheter 42. Preferably, the inside of the distal end 52 is sized for a close fit over the outside of catheter 42. The hemostasis sheath 50 also has a proximal end 54 opposite from the distal end 52. The proximal end 54 has a larger outside diameter than the distal end 52. Preferably, the proximal end 54 has an outside diameter which is about at least as large or slightly larger than the outside diameter of the IAB bladder 40 in its wrapped condition.

Figure 3:
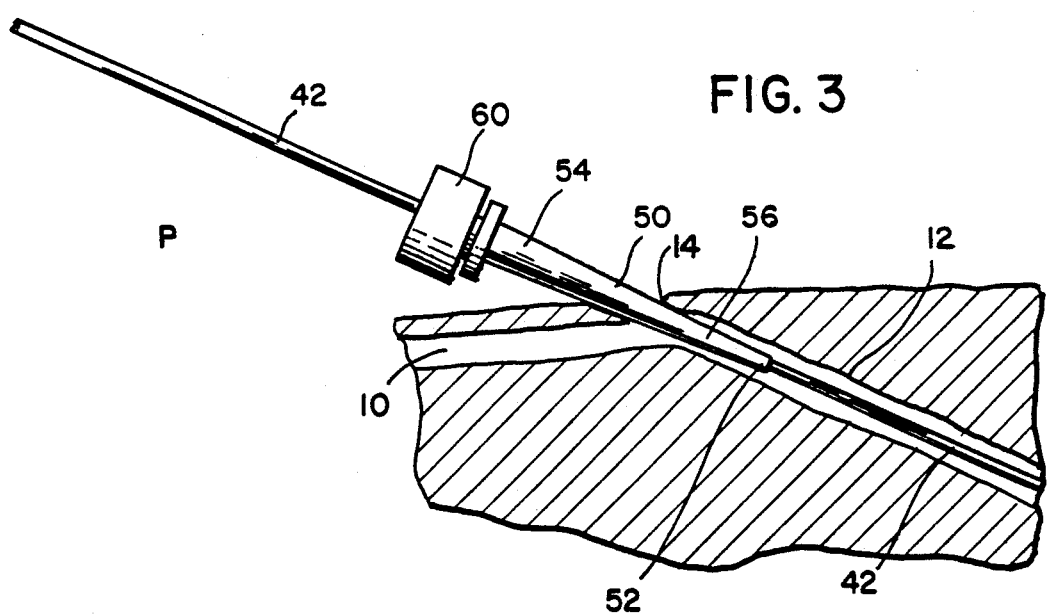
FIG. 3 is a side elevation view of the IAB device of FIGS. 1 and 2 showing the hemostasis sheath of the present invention positioned within the insertion puncture.

FIG. 3 shows from left to right the IAB catheter 42 and hemostasis sheath 50 of FIGS. 2a and 2b with the hemostasis sheath 50 now positioned in the insertion site 8.

With reference to FIG. 3, the hemostasis sheath 50 has now been inserted partially into the opening 14 in the wall of the artery 10 with its distal end 52 extending inside the artery 10. The hemostasis sheath 50 is inserted into the artery 10 until the point is reached where its increased diameter at point 56, between the distal and 52 and proximal end 54, fills the opening 14. As shown in FIG. 3, the hemostasis sheath 50 is thereby able to stop the bleeding which might have resulted after insertion of the IAB device. Additionally, the hemostasis sheath 50 is configured and dimensioned to pass through the skin 20 and into the artery 10, and is able to control bleeding without restricting good blood flow through the artery 10 to any great degree.

In accordance with the inventive method, the hemostasis sheath 50 is advanced along the balloon catheter 42 through the skin and into the artery by a sufficient distance to control bleeding from the insertion site 8. In particular, the hemostasis sheath 50 is advanced to a point where its outside diameter sufficiently fills the opening made by the passage of the IAB bladder through the skin and artery to provide an elastic contact between the skin opening and the outside diameter of the hemostasis sheath 50.

Figure 4:
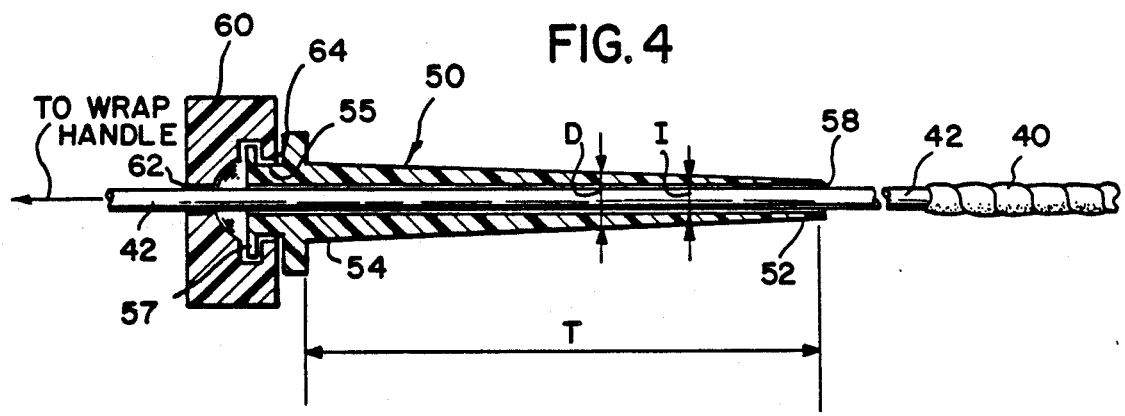
FIG. 4 is a cross-section of the hemostasis sheath according to the invention showing the hemostasis sheath installed on a balloon catheter.
Figure 5:
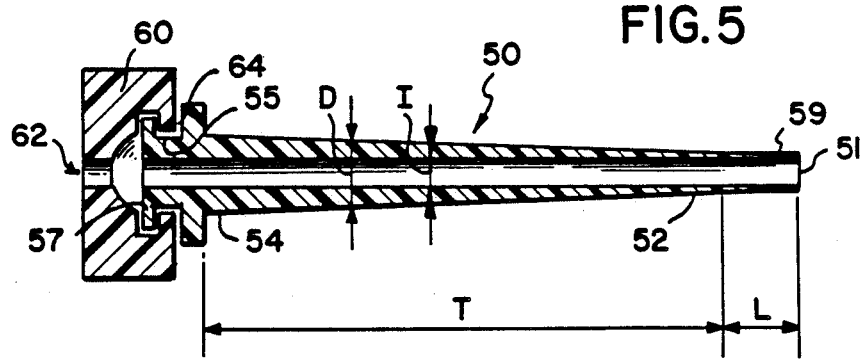
FIG. 5 is a cross-section of another embodiment of the hemostasis sheath according to the invention.
Figure 6:
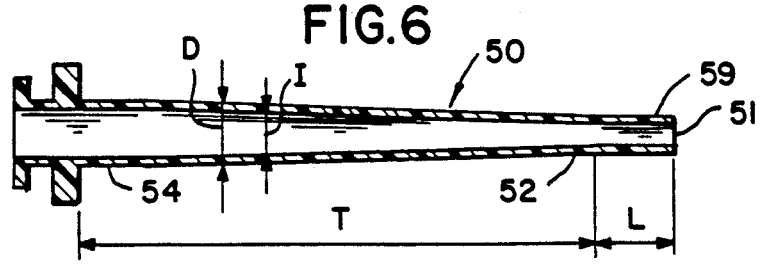
FIG. 6 is a cross-section of yet another embodiment of the hemostasis sheath according to the invention showing an inside diameter which gradually increases from the distal end to the proximal end.

The hemostasis sheath 50 is shown in greater detail in FIGS. 4, 5 and 6. Unless otherwise indicated, FIGS. 4, 5 and 6 show, from left to right the IAB catheter 42 (FIG. 4 only) a cuff 60 and hemostasis sheath 50. Additionally, from left to right, the hemostasis sheath comprises a flange 57, a neck 55, proximal end 54, distal end 52 and an extended portion 59 including a tip 51.

The outside diameter (D) of the hemostasis sheath 50 gradually increases from its distal end 52 towards its proximal end 54. The inside diameter (I) of the hemostasis sheath 50 may be about the same throughout its entire length (as shown in FIGS. 4 and 5) or may gradually increase from the distal end 52 towards the proximal end 54 (as shown in FIG. 6, for example). Preferably, the inside diameter (I) is sized at the distal end 52 to provide a close clearance 58 between the inside of the hemostasis sheath 50 and the outside of the balloon catheter 42. Preferably the inside diameter (I) of the hemostasis sheath 50 at its distal end 52 is between about 2 to 3 thousandths of an inch larger than the outside diameter of the balloon catheter 42 to allow for manufacturing tolerance. More preferably, in view of the resilience of the materials utilized, one can maintain an interference fit such that the distal end 52 the inside diamter (I) of the hemostasis sheath 50 is the same as the outside diameter of the balloon catheter 42. This close fit clearance 58 permits the outside diameter of the hemostasis sheath 50 to be as small as possible at the distal end 52 with the balloon catheter 42 providing structural support for the hemostasis sheath 50 during insertion to prevent an accordian effect from occurring at the distal end 52. This close fit clearance also reduces the risk of bleedblock between the bladder catheter 42 and the hemostasis sheath 50.

For example, in a preferred embodiment wherein the outside diameter of the balloon catheter is about 10.5 french (i.e., about 0.138 inches), the outside diameter (D) of the hemostasis sheath 50 at its distal end 52 is about 0.146 inches, the outside diameter (D) at its proximal end 54 is about 0.185 inches and the inside diameter (I) of the hemostasis sheath 50 at the distal end 52 is about 0.140 inches to provide a clearance 58 of about 0.002 inches at the distal end 52.

Preferably, the outside diameter (D) of the hemostasis sheath 50 tapers gradually from its distal end 52 to its proximal end 54 and the distance (T) between the distal end 52 and proximal end 54 is preferably about 2.0 to 2.5 inches. Of course, the outside diameter may also increase in a step-wise manner (not shown). By "gradual" is meant any shape which increases in outside diameter in a continuous, as opposed to step-wise, manner. Such gradual shapes include cones having straight sides along their length or curved sides.

As shown in FIGS. 5 and 6, in another preferred embodiment, the distal end 52 of the hemostasis sheath 50 may further include constant diameter portion 59.

The constant diameter portion 59 would preferably have a length of at least about ¼ inch and an inside diameter which is about 2 to 3 thousandths of an inch larger than the outside diameter of the balloon catheter 42.

The constant diameter portion 59 is configured to generate less initial resistance during insertion through the skin so that the tip 51 of the hemostasis sheath 50 can be more easily inserted. Once the constant diameter portion 59 has been inserted through the skin, the overall resistance to further insertion will increase as the outside diameter of the hemostasis sheath 50 increases. However, with the tip 51 safely passed through the skin, the danger of collapsing or buckling as an accordian at the tip 51 can be avoided.

The hemostasis sheath 50 is provided at its proximal end with a neck 55 and flange 57. The neck 55 and flange 57 are held within the cuff 60. As shown in FIGS. 4 and 5, the cuff 60 is sized to provide a close clearance 64 between the cuff 60 and neck 55 of the hemostasis sheath 50. Additionally, the cuff 60 is sized to provide a close clearance 62 between the cuff 60 and the balloon catheter 42. In this manner, the cuff 60 is able to seal the proximal end of the hemostasis sheath 50 against bleeding when the distal end 52 is positioned within the femoral artery 10. Closed clearance 62 also precludes slippage of cuff 60 and, in turn, hemostasis sheath 50 along catheter 42 due to arterial pressure and the like.

In a preferred embodiment, the hemostasis sheath 50 is manufactured from a resilient, for example plastic, material, which is preferably polytetrafluoroethylene (Teflon ®) or polyethylene. Also in the preferred embodiment, the cuff 60 is manufactured from an elastomeric material, for example silicone. However, no particular elastomeric material is preferred.

The various features and advantages of the invention are thought to be clear from the foregoing description. Various other features and advantages not specifically enumerated will undoubtedly occur to those versed in the art as likewise will many variations and modifications of the preferred embodiment illustrated, all of which may be achieved without departing from the spirit and scope of the invention as defined by the following claims.

We claim:

1. A method for inserting an intra-aortic balloon apparatus through a patient's skin and into the femoral artery, wherein said intra-aortic balloon apparatus includes a balloon catheter having a proximal end and a distal end, an inflatable and deflatable balloon bladder means sealidly attached at the distal end of the balloon catheter and a hollow stylette means passing through the length of the intra-aortic balloon, said intra-aortic balloon apparatus further including a hemostasis sheath slidably coupled with the balloon catheter between the balloon bladder means and the proximal end of the balloon catheter, said hemostasis sheath having a distal end adjacent to the balloon bladder means and a proximal end opposite from the balloon bladder means having a larger outside diameter than that at the distal end, said intra aortic balloon apparatus also including sealing means releaseably coupled to said hemostasis sheath, the method comprising the steps of:

(a) puncturing the patient's skin and femoral artery to create an opening in the skin and artery;
(b) inserting a guide wire into the opening in the artery and passing the guide wire up to the patient's aorta;
(c) dilating with dilating means the opening to achieve a diameter sufficient to permit insertion of the intra-aortic balloon bladder means in a wrapped configuration into the femoral artery;
(d) removing the dilating means;
(e) without the use of an insertion sheath, directly inserting the intra-aortic balloon bladder means in a wrapped configuration over the guide wire and through the opening and passing it up to the aorta; and
(f) sliding the hemostasis sheath along the balloon catheter, through the insertion site and into the femoral artery far enough to control bleeding from the puncture opening in the femoral artery, yet permit blood flow along the femoral artery.

2. The method of claim 1 further including the step of securing the sealing means to the hemostasis sheath after the hemostasis sheath is slid through the insertion site to preclude bleeding between the hemostasis sheath and the balloon catheter.

3. The method according to claim 1, including the step of selecting the hemostasis sheath such that it is gradually tapered to decrease from its proximal end to its distal end.

4. The method according to claim 1, wherein the dilating step (c) comprises sliding the dilating means along the guide wire into the opening so as to dilate the opening.

5. The method according to claim 4, wherein the dilating step (c) comprises selecting a tapered dilater having an outside diameter increasing from its distal end closest to the artery to a larger outside diameter at its proximal end away from the artery.

6. The method according to claim 5, further including the step of selecting the hemostasis sheath such that it is gradually tapered to decrease from its proximal end to its distal end.

7. The method according to claim 6, further including the step of selecting the hemostasis sheath having an inside diameter which is slightly larger than the outside diameter of the balloon catheter with a clearance therebetween of about 2 to 3 thousandths of an inch at least at the distal end of said hemostasis sheath.

8. The method according to claim 6, further including the step of selecting the dilating means such that it is gradually tapered.

9. A method for inserting an intra-aortic balloon apparatus through a patient's skin and into the femoral artery, wherein said intra-aortic balloon apparatus includes a balloon catheter having a proximal end and a distal end, an inflatable and deflatable balloon bladder means sealidly attached at the distal end of the balloon catheter and a hollow support means passing through the length of the intra-aortic balloon apparatus, said intra-aortic balloon apparatus further including a hemostasis sheath slidably coupled with the balloon catheter between the balloon bladder means and the proximal end of the balloon catheter, said hemostasis sheath having a distal end portion adjacent to the balloon bladder means and a proximal end portion opposite from the balloon bladder means having a larger outside diameter than at the distal end portion, said intra-aortic balloon apparatus also including sealing means for precluding blood flow between the hemostasis sheath and the balloon catheter, the method comprising the steps of:
(a) puncturing the patient's skin and femoral artery to create an opening in the skin and artery;
(b) inserting a guide wire through the opening and into the femoral artery;
(c) dilating with dilating means the opening to achieve a diameter sufficient to permit insertion of the balloon bladder means in a deflated condition into the femoral artery;
(d) removing the dilating means;
(e) without the use of an insertion sheath, directly inserting the balloon bladder means in a deflated condition over the guide wire and through the opening and passing it up to the aorta;
(f) sliding the hemostasis sheath along the balloon catheter, through the opening and into the femoral artery far enough to control bleeding from the opening; and
(g) engaging the sealing means to the proximal end of the hemostasis sheath to preclude blood flow between the balloon catheter and the hemostasis sheath.

10. The method of claim 9 further including the step of selecting the hemostasis sheath such that it has an inner diameter at least at its distal end portion just sufficient to permit the hemostasis sheath to slide along the balloon catheter.

11. The method of claim 9 further including the step of selecting the hemostasis sheath such that its outside diameter is just larger than its inner diameter at the distal end portion of the hemostasis sheath and, at the proximal end portion of the sheath its outside diameter is predetermined to be at least as large as the opening in the patient's skin and femoral artery.

12. The method of claim 11, further including the step of selecting the hemostasis sheath such that its outside diameter is tapered to increase in a direction from the distal end portion toward the proximal end portion of the hemostasis sheath.

13. The method of claim 12 further including the step of selecting the hemostasis sheath such that its outside diameter tapers along the length of the hemostasis sheath.

14. The method of claim 12 further including the step of selecting the hemostasis sheath such that it has a conical configuration.

15. The method of claim 11 further including the step of selecting the sealing means to have a configuration such that the sealing means is releasably secured to the proximal end of the hemostasis sheath, and the sealing means has an inner diameter just sufficient for the sealing means to slide along the balloon catheter yet preclude blood flow between the inside diameter of the sealing means and the balloon catheter.

16. A method of claim 15 further including the step of selecting a cuff as the sealing means.

17. A method for inserting an intra-aortic balloon apparatus through a patient's skin and into the femoral artery, wherein the intra-aortic balloon apparatus includes a balloon catheter having a proximal end and a distal end, an inflatable and deflatable balloon bladder means sealidly attached at the distal end of the balloon catheter and a hollow support means passing through the length of the intra-aortic balloon apparatus, said intra-aortic balloon apparatus further including hemostasis means slidably disposed on the balloon catheter between the balloon bladder means and the proximal end of the balloon catheter for controlling bleeding, the method comprising the steps of:

(a) puncturing the patient's skin and femoral artery to create an opening in the skin and artery;

(b) inserting a guide wire through the opening and into the femoral artery;

(c) dilating with dilating means the opening to achieve a diameter sufficient to permit insertion of the balloon bladder means in a deflated condition into the femoral artery;

(d) removing the dilating means;

(e) without the use of an insertion sheath, directly inserting the balloon bladder means in a deflated condition over the guide wire and through the opening and passing it up to the aorta; and (f) sliding the hemostasis means along the balloon catheter, through the opening and into the femoral artery far enough to control bleeding from the opening.

18. The method of claim 17 further including the step of selecting the hemostasis means such that the hemostasis means has a distal end portion adjacent the balloon bladder means, a proximal end portion opposed to the balloon bladder means, and an outside diameter just larger than the outside diameter of the balloon catheter at the distal end portion, and said outside diameter of the hemostasis means increasing in a direction toward the proximal end portion of the hemostasis means to a size which is at least as large as the opening in the patient's skin and femoral artery.

19. The method of claim 18 further including the step of selecting the hemostasis means such that it has an inner diameter at least at the distal end portion of the means just sufficient to permit the hemostasis means to slide along the balloon catheter, and an outer diameter which is just larger than the inner diameter at the distal end portion of the hemostasis means, said outside diameter tapering in a direction toward the proximal end portion of the hemostasis means such that it becomes at least as large as the patient's opening in the skin and femoral artery.

20. The method of claim 18 further including the step of selecting the hemostasis means such that it has a conical configuration.

21. The method of claim 18 further including the step of selecting a sealing means for engaging the proximal end of the hemostasis means to preclude blood flow between the hemostasis means and the balloon catheter, said sealing means having an inner diameter just sufficient for the hemostasis means to slide along the balloon catheter yet permit blood to flow through so as to prevent blood flow between the balloon catheter and the hemostasis means.

* * * * *